(12) United States Patent
Samuelsson et al.

(10) Patent No.: US 6,508,795 B1
(45) Date of Patent: Jan. 21, 2003

(54) ABSORBENT ARTICLE WITH IMPROVED LIQUID ACQUISITION CAPABILITY

(75) Inventors: Ann Samuelsson, Lindome (SE); Charlotte Persson, Göteborg (SE)

(73) Assignee: SCA Hygiene Products AB, Göteborg (SE)

( * ) Notice: Subject to any disclaimer, the term of this patent is extended or adjusted under 35 U.S.C. 154(b) by 0 days.

(21) Appl. No.: 09/445,189

(22) PCT Filed: Jun. 18, 1998

(86) PCT No.: PCT/SE98/01186

§ 371 (c)(1),
(2), (4) Date: Dec. 8, 1999

(87) PCT Pub. No.: WO98/58613

PCT Pub. Date: Dec. 30, 1998

(30) Foreign Application Priority Data

Jun. 24, 1997 (SE) ............................................ 9702395-6

(51) Int. Cl.[7] ............................................... A61F 13/15
(52) U.S. Cl. ............................. 604/378; 604/385.101; 604/385.11; 604/385.14
(58) Field of Search ................. 604/378, 379, 604/385.01, 385.101, 385.16, 385.23, 385.11, 385.14

(56) References Cited

U.S. PATENT DOCUMENTS

| | | | |
|---|---|---|---|
| 4,501,586 A | 2/1985 | Holtman | 604/380 |
| 4,961,736 A | * 10/1990 | McCloud | 604/385.1 |
| 5,197,959 A | * 3/1993 | Buell | 604/385.1 |
| 5,318,553 A | 6/1994 | Weeks et al. | 604/378 |
| 5,403,302 A | * 4/1995 | Roessler et al. | 604/391 |
| 5,582,603 A | 12/1996 | Difilippantonio et al. | 604/380 |
| 5,591,148 A | 1/1997 | McFall et al. | 604/378 |
| 5,695,324 A | * 12/1997 | Weirch | 604/378 |
| 5,756,039 A | * 5/1998 | McFall et al. | 264/118 |
| 5,830,202 A | * 11/1998 | Bogdanski et al. | 604/368 |
| 5,947,945 A | * 9/1999 | Cree et al. | 604/368 |
| 5,947,947 A | * 9/1999 | Tanzer et al. | 604/385.1 |
| 6,114,597 A | * 9/2000 | Romare | 604/378 |

FOREIGN PATENT DOCUMENTS

SE         507 798         11/1996

* cited by examiner

Primary Examiner—Glenn K. Dawson
Assistant Examiner—Jamisue A. Webb
(74) Attorney, Agent, or Firm—Burns, Doane, Swecker & Mathis, LLP (57) ABSTRACT

An absorbent article such as a sanitary napkin, an incontinence pad, panty liner or the like, which article is intended to be substantially accommodated within a user's panties and comprising an absorbent upper part (2) and an absorbent lower part (3), which two parts are mutually joined in such a manner that the article, at least in its mid portion (26), presents an elongate cavity between the upper part (2) and the lower part (3) which is maintained during use.

37 Claims, 6 Drawing Sheets

ABSORBENT ARTICLE WITH IMPROVED LIQUID ACQUISITION CAPABILITY

TECHNICAL FIELD

The present invention relates to an absorbent article such as a sanitary napkin, a panty liner or an incontinence pad, which article is intended to be substantially accommodated within the panties of a user and comprising a first absorbent part and a second absorbent part, which two parts are mutually joined.

BACKGROUND OF THE INVENTION

A basic requirement for an absorbent article such as a sanitary napkin or the like is that the article must be shaped in such a manner that it can collect and absorb all discharged bodily fluid.

Since, for example, sanitary napkins are intended to be accommodated within a pair of normal panties, they are relatively small and, above all, often rather narrow. There is therefore an obvious risk that by misplacing such an article within the panties or by it being deformed during use, it will not present a sufficiently large receiving surface for the discharged bodily fluid.

For example, it is not uncommon that the absorbent article is placed by mistake too far forward or too far backwards or offset somewhat transversely. Another commonly occurring reason for bodily fluid to leak past an absorbent article and to soil the user's clothing is that the article is compressed between the legs of the user and thus becomes so narrow that the surface available for absorption becomes insufficient. Neither is it unusual for the side edges of the article to become folded over the surface of the article, thereby reducing the available surface.

An absorbent article of the type under consideration is generally maintained in the panties of the user by means of self-adhesive glue and/or a friction coating. When placing the article in the panties, it is difficult to obtain a placement which is optimal in relation to the body of the user. Normally, the crotch portion of the panties is used to determine where the article is to be placed. However, since panties are manufactured in a surprisingly large number of different models and sizes, the position and shape of the central portion provides an extremely unreliable indication of where in the panties an absorbent article should be positioned.

One way to reduce the risk of edge leakage due to deformation of the article during use is to provide the article with a preformed raised portion which, during use, is intended to contact the user is genitals. In this manner, discharged bodily fluid can be intercepted as soon as it exits the user's body and be immediately absorbed within the article instead of running over its surface. In addition, a raised portion facilitates the placement of the absorbent article by the user in a correct position in relation to the body.

For this purpose, a raised portion of the type which is described in Swedish patent application no. 9604221-3 is particularly suitable. Such a raised portion has a predictable shape both before and during use and it maintains its shape irrespective of the movements of the user and the wetting to which the article is subjected. The raised portion is anatomically shaped, which implies that it is relatively narrow so as to be able to be inserted somewhat between the labia of the user during use without causing discomfort to the user.

Even though such a raised portion functions well for its purpose, it has been shown that should the raised portion be subjected to large quantities of bodily fluid during a relatively short period of time, there is a risk that a quantity of the liquid will run down on the outside of the raised portion and over the side edges of the absorbent article. For example, such leakage can arise when the user of a sanitary napkin has been sitting or lying down for a long period of time and then suddenly gets up. When the user has been sitting or lying down, a relatively large quantity of menstrual fluid may collect in the user's vagina. As a result of a sudden change in the body position, the entire quantity of collected fluid can be discharged in one go. A narrow raised portion of the type which is described in SE 9604221-3 does not therefore have a sufficiently large surface to be able to receive and absorb the entire quantity of liquid at once, which is why such sudden liquid flows often result in leakage.

SUMMARY OF THE INVENTION

However, by means of the present invention an improved absorbent article of the above-mentioned type has been provided in which the risk of leakage has been considerably reduced.

An article in accordance with the invention is primarily characterized in that the article comprises means for obtaining and maintaining an elongate cavity between the second surface of the upper part and the first surface of the lower part, at least in the wetting region which is that region of the article which is intended to initially receive discharged bodily fluid, whereby the upper part and the lower part are separated from each other by a distance of between 0.3 mm and 5 mm in the elongate cavity and that the elongate cavity permits liquid transmission in between the upper part and the lower part. For liquid to be able to enter between the two constituent parts of the article, it is therefore necessary that the edge regions of the parts are maintained at a distance from each other, at least in the wetting region of the article.

According to one embodiment of the invention, the upper part is substantially made from a relatively stiff material and is substantially elongate and presents a first end section and a second end section, whereby the upper part is connected to the lower part solely at the end sections. Furthermore, the lower part comprises a rigid, shape-permanent material layer which has at least the same extension in the principal plane of the article as the upper part, whereby the shape-permanent material layer is curved in the article's longitudinal direction in a direction away from the upper part, whereby the first surface of the lower part is also curved in a direction away from the upper part, with the second surface of the upper part having a shape such that the article presents a gap between the upper part and the lower part.

In such an embodiment, the elongate cavity is created and maintained by the presence of the curved, shape-permanent material layer as well as by the upper part also having relatively high stiffness. High stiffness in the upper part can be obtained, for example, by using a heavily compressed absorption material or by a particular stiffness-increasing insert of metal, plastic, wood or the like. In addition, the surface on the upper part which faces towards the lower part must be shaped so that it creates a gap between the upper part and the lower part. This implies that the second surface of the upper part can be curved in the same direction as the first surface of the lower part, though with a greater radius of curvature than the lower part. Alternatively, the second surface of the upper part can be completely flat or can be curved in a direction away from the lower part. Combinations of different curvatures within different parts of the curved surfaces are conceivable as long as an elongate cavity is maintained between the two parts, at least within the wetting region of the article.

For example., the shape-permanent material layer can advantageously be curved in a direction away from the upper part in both the longitudinal and the transverse direction of the article, whereby the lower part is bowl-shaped at least in the article's wetting region and thereby creates a liquid-receiving container under the upper part of the article.

If the shape-permanent material layer is made from liquid impermeable material such as plastic or the like, the shape-permanent material layer can form the liquid impermeable layer of the lower part and thereby form a liquid impermeable bottom layer of the article. Such a shape-permanent, liquid impermeable shell can also be used to give the article a predetermined, anatomically adapted shape.

Considering the comfort of the user, since the shape-permanent material layer is made of a very stiff and hard material, it is suitable that the shape-permanent material layer at least somewhere within the mid portion of the article has a greatest extension in the article's transverse direction which does not exceed 40 mm, and preferably does not exceed 35 mm.

It can furthermore be suitable to arrange soft, pressure-absorbing deformation zones around at least parts of the article's side edges.

Another method of attaining a gap-like cavity between the upper and lower parts of the article is by arranging a spacer between the parts. Such a spacer can, for example, be in the form of a snap fastener, a material plate, or the like. The spacer should be substantially unaffected by wetting and at least should not collapse so that the elongate cavity would disappear when the article is being used. Suitable materials for use as such a spacer are, for example, plastics, metal, wood, or absorbent material which swells rather than collapses when wetted.

A further example of a spacer which can be used is a stiffening element arranged substantially perpendicular to the bottom layer of the lower part and which extends from the bottom layer through the lower part and onwards into the upper part.

The upper part can be fixedly attached to the lower part or may be attached to the lower part in a manner which allows the upper part to be released from the lower part. The advantage with the latter embodiment is that it is thereby possible to remove a soiled upper part while reusing the lower part. In addition, the user is given the possibility to determine herself whether she wishes to use the upper part.

In accordance with a further embodiment, the connection between the upper part and the lower part is such that it permits repeated attachment and separation of the two parts. Examples of attachment devices which permits repeatable attachment and separation are hook-and-loop type surfaces, crooks/hooks, loops, buttons, snap fasteners or the like.

In order to provide the absorbent article with an anatomically correct shape it is suitable that the upper part has an extension in the article's transverse direction which is less than the extension of the lower part in the transverse direction. A particularly advantageous size-ratio is realized if the width of the mid portion of the upper part is between ¼ and ⅓ of the width of the lower part.

In a corresponding manner, the upper part should have a lesser extension in the longitudinal direction than the lower part and should thereby be between ⅓ and ¾ of the length of the lower part.

By arranging the two constituent parts of the article at a distance from each other, it is possible in a second absorption stage to collect bodily fluid which flows over the outside of the first part. In this manner, it is avoided that the bodily fluid flows past the edges of the article to thereby result in leakage. Instead, the bodily fluid can flow in under the first part and be absorbed by the absorption material in the second part. It is thereby suitable that the second part of the absorbent article is bowl-shaped or curved in the article's transverse direction so that the fluid flows under the influence of gravity towards the longitudinal centerline of the article, i.e. in under the first part.

BRIEF DESCRIPTION OF THE DRAWINGS:

The invention will be described in the following in greater detail with reference to embodiments shown in the attached drawings. Thus.

Figure 1:
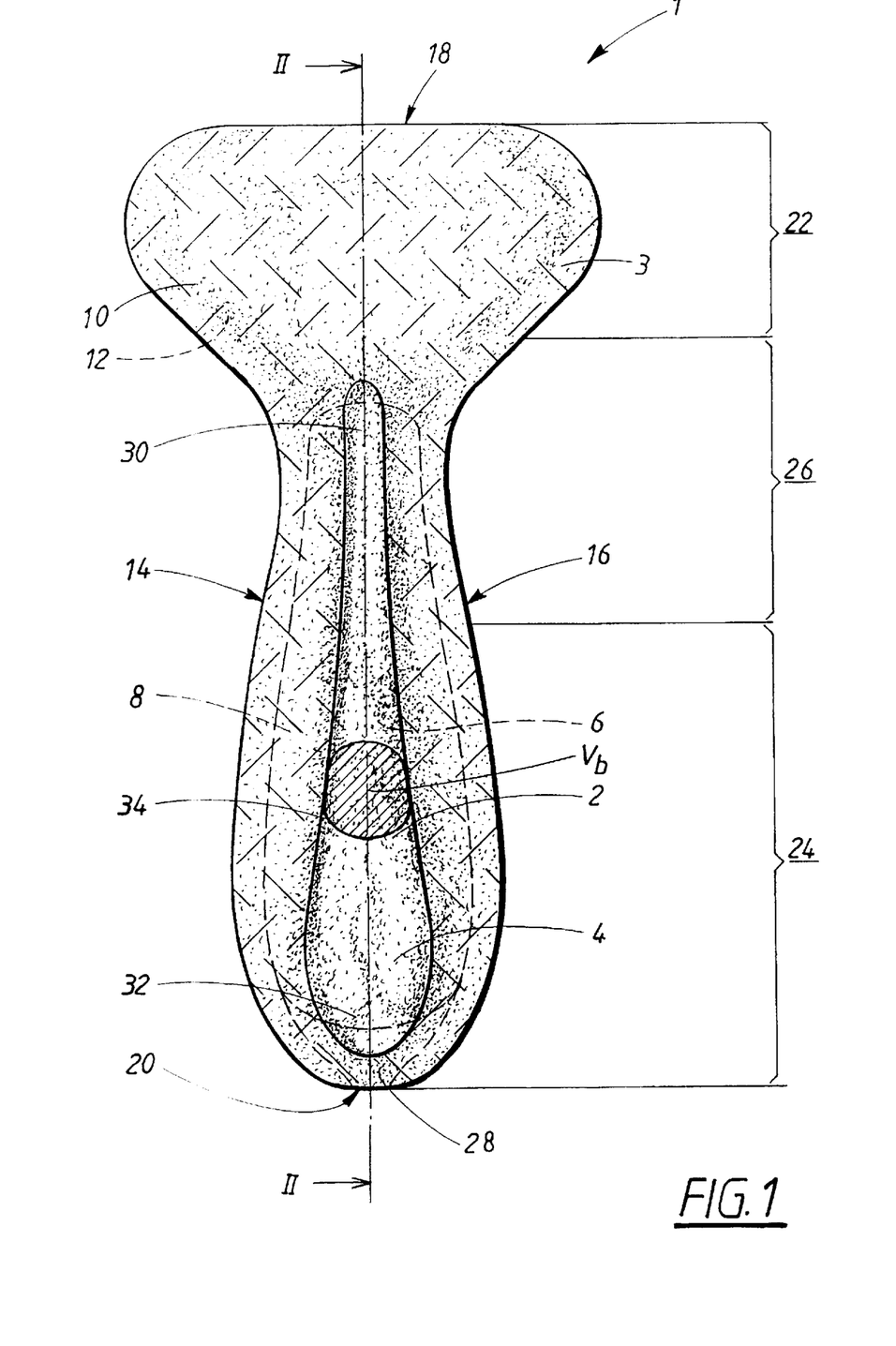
FIG. 1 shows a sanitary napkin seen from the side which, during use, is intended to face the user.
Figure 2:
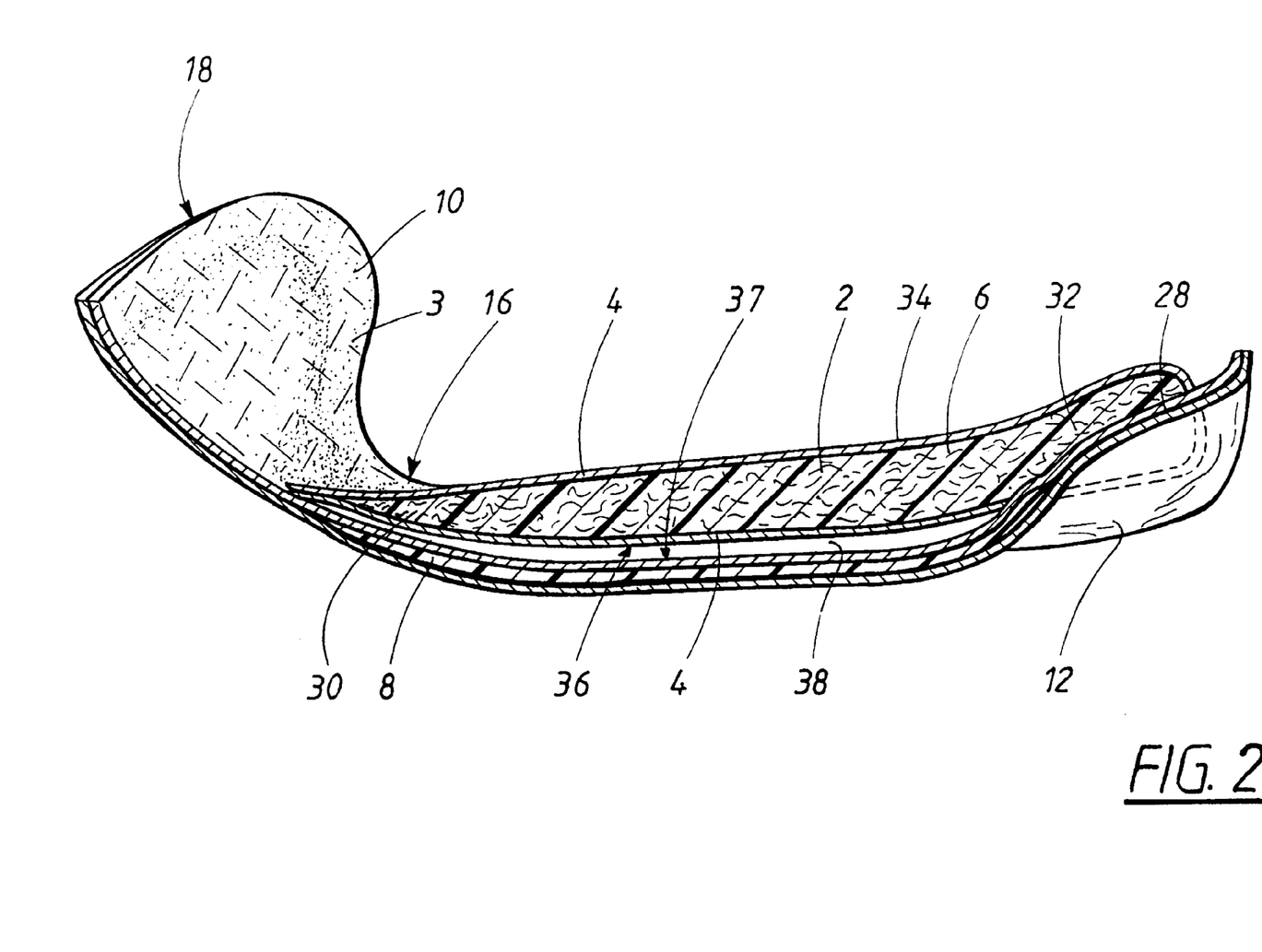
FIG. 2 is a section along line II—II of the sanitary napkin of FIG. 1.

DETAILED DESCRIPTION OF PREFERRED EMBODIMENTS:

The sanitary napkin 1 shown in FIGS. 1 and 2 is made from two parts 2, 3. The upper part 2 is absorbent and is intended to contact the user's body during use and collect and absorb the majority of the bodily fluid which is discharged onto the sanitary napkin. The upper part 2 comprises a wrapping 4 of liquid-permeable material. The wrapping 4 encases an absorbent body 6 which is dimensioned to be able to receive and absorb the majority of the bodily fluid which is discharged to the sanitary napkin during use.

The liquid-permeable material of the wrapping 4 is suitably a soft, skin-friendly and flexible material of the type which is commonly used as surface material on absorbent articles. Examples of such materials are perforated plastic films, nonwoven textiles normally known as nonwoven material, nets of textile or plastic made by stitching, crocheting, braiding, moulding or the like and, of course, conventional woven textile materials.

The absorbent body 6 can be of any type suitable for the stated purpose. Thus, the absorbent body 6 can also be made from one or more layers of absorbent fibres, such as cellulose-fluff pulp, rayon, cotton or the like, as well as tissue material, nonwoven material, foam or other absorbent or non-absorbent components.

In order to increase the absorption capacity, the absorbent body 6 can contain so-called superabsorbents which are polymer materials normally present in the form of particles, flakes, fibres or the like and with the capability to absorb several times their own weight of bodily fluid during formation of an aqueous gel. Superabsorbents can be present as one or more layers or regions in the absorbent body 6, or may be mixed with other absorbent material such as cellulose fluff pulp or absorbent fibre waddings of another type. Of course, the superabsorbent may also be present in a non-absorbent support structure, for example a fibrous layer of non-absorbent fibres.

In order to attain sufficient shape-retention in the sanitary napkin's upper part 2, it is necessary that at least some component in the upper part 2 is stiff and inflexible so that the upper part maintains its shape during use. Sufficient stiffness can be achieved by heavy compression of the absorbent material, by use of a particular shape-retaining and stiffness-enhancing insert or through selection of an absorbent material with high shape-permanence and stiffness. Of course, it is possible to combine different materials so that sufficient stiffness is attained.

One type of absorbent material which has been shown to be particularly suitable for this purpose is described in WO 94/10953 and WO 94/10956. These materials are in the form of dry-defibrated fibre layers of high density and stiffness. The density ought to be between 250–200 g/cm$^3$ and preferably between 350–100 g/cm$^3$. The fibre layers are used directly in an absorbent article without previous defibration. The fibre layers have high stiffness and the ability to withstand pressure deformation, whereby an absorbent body 6 comprising such material has good shape retention. In addition, the fibre materials have very good absorption capacity.

The upper part 2 is shaped so as to be able to contact the genitals of the user and should have sufficient absorbent capacity for all discharged bodily fluid to be able to be absorbed by the absorbent body 6.

As with the upper part 2, the lower part 3 of the sanitary napkin comprises an absorbent body 8 which is encased in a wrapping. Thereby, the wrapping consists of a liquid-permeable surface layer 10 which faces towards the upper part 2, as well as a liquid-impermeable bottom layer 12 which, during use, faces away from the user.

The liquid-permeable surface layer 10 is advantageously made from any one of the materials mentioned above for the wrapping 4 of the upper part 2. In FIGS. 1 and 2, the liquid-permeable surface layer 10 is shown having a binding pattern. The purpose of this is to indicate that it is possible to choose a material partially having other properties than the material of the upper part's liquid-permeable wrapping. Since, during use, the upper part 2 may come into contact with the sensitive mucous membranes between the user's labia, it can be suitable for the wrapping 4 to consist of a smooth, even material without prominent binding pattern. In addition, it may be desirable that the surface of the wrapping 4 which, during use, can be expected to contact the mucous membranes has certain absorbent capacity. In this manner, a certain amount of moisture will remain in the wrapping. The risk of drying out and irritation of the mucous membranes will thus be reduced. The liquid-permeable surface layer 10 on the lower part 3 will, during use, be substantially in contact with the user's skin. Such a surface layer 10 should therefore be soft and airy and substantially non-absorbent. In this manner, a surface layer is provided which keeps the skin dry and which does not mechanically chafe or in any other way irritate the skin. One way of attaining a soft and airy surface layer is by using a nonwoven material having a relatively widely distributed binding pattern, for example of the type which is shown in FIG. 1. However, the invention is not to be regarded as being restricted to the shown binding pattern or to the use of nonwoven material as the surface layer of the lower part 3. For example, it is possible to attain very dry surface materials with different types of perforated plastic films, plastic nets or laminates.

The liquid-impermeable bottom layer 12 of the lower part consists of a liquid-impermeable shape-permanent shell of a stiff material, preferably plastic. The material in the bottom layer 12 should therefore be selected so that the bottom layer 12 substantially resists compression and deformation in the transverse direction of the sanitary napkin during use.

The sanitary napkin 1 shown in FIGS. 1 and 2 has a substantially elongate shape with two longitudinal side edges 14, 16 and two transverse end edges 18, 20. Furthermore, the sanitary napkin presents a relatively wide, bowl-shaped forward portion 22, a rounded, raised rearward portion 24 and an intermediate mid portion 26.

At least in the sanitary napkin's mid portion 26, the lower part 3 is comparatively narrow with respect to its length and thus has a width which is suitably between 1 and 4 cm and preferably about 3 cm. Measurements have shown that there is a space-limiting, critical region in the groin region between two muscle groups which extend from the inside of the pelvic floor and down each thigh. The distance between the two muscle groups in the genital region has thus been found to be surprisingly similar for all people, irrespective of body shape and corpulence. Thus, the distance between the user's thighs will of course be affected by body fat, whilst the distance between the muscle groups in the user's crotch is substantially the same irrespective of whether the user is thin, of normal weight or overweight.

It has been shown by measurements that the determining factor as to whether a user experiences discomfort in the form of pressure or chafing on the insides of the thighs is whether the absorbent article during use has a width which, in the critical region, obviously exceeds the distance between the muscle groups in the groin region. This distance has been shown to be between 30 and 35 mm. It has furthermore been shown that an article having a width which, during use, exceeds 40 mm in the critical region is regarded by many users as being uncomfortable to wear. However, that an absorbent article was pressed towards or projected under the fatty tissue which can be present in the groin region was rarely regarded as uncomfortable. With conventional absorbent articles, the restricted space in the user's crotch implies that the article is compressed in an uncontrolled manner between the user's legs and becomes folded so as to be able to be accommodated in the groin. However, should some component of the absorbent article have such a stiffness that it cannot easily be compressed by the forces which normally arise during use, the compression can of course only take place to a restricted extent. For reasons of comfort, therefore, it is important that the width of the absorbent article in the mid portion during use does not exceed the critical value which can be tolerated by the user. A certain controlled compressibility can be achieved by providing the article with deformable zones. Such deformable zones can for example be in the form of soft edges, longitudinally extending material folds or material weakenings such as holes, thinner material regions or the like.

It is, of course, the width of the article during use which is relevant for the determination of whether or not the risk of chafing arises. Soft components which are deformed during use do not therefore contribute to the same extent to the width of the article during use as relatively non-deformable components would do.

As has previously been mentioned, the material which is used for the liquid-impermeable layer in the lower part 3 is advantageously so stiff that it cannot be deformed in the transverse direction by the compressive forces which arise between the user's thighs. It is therefore important that the width of the liquid-impermeable layer at least in the region which, during use, is intended to be in the critical region between the user's legs, does not exceed 40 mm and preferably does not exceed 35 mm. Plastic films which have been shown to be suitable for use in the liquid-impermeable bottom layer 12 are, for example, layers of polyethylene plastic, filled polypropylene plastic or polyester having a thickness of between 0.5 mm and 1 mm.

In the sanitary napkin 1 shown in FIGS. 1 and 2, the shape of the napkin is maintained by the entire liquid-impermeable bottom layer 12 being a shape-permanent shell for the remaining components of the sanitary napkin. The bottom layer 12 is curved in both the longitudinal direction and the transverse direction in order to give the sanitary napkin an anatomically correct shape. Thus, the forward portion 22 is angled upwards in a direction towards an imaginary user and curved transversely. In this manner, a softly rounded bowl is attained which fits the shape of the user's pubic mons. In a corresponding manner, the bottom layer 12 is shaped with a raised portion 28 at the rearward portion 24 of the sanitary napkin. The raised portion 28 in the rearward portion 24 is thereby intended to fit into the space beyond the user's vaginal opening and be accommodated in the forward portion of the furrow between the user's buttocks. As a result of the anatomically adapted shape of the sanitary napkin, it can be maintained during use between the user's legs in contact with the user's body without the need for any particular fastening means.

The upper portion 2 of the sanitary napkin is elongate and relatively narrow. The upper part 2 also presents a forward section 30 and a rearward section 32. In order to fit the user's anatomy in the region in question, the upper part 2 is shaped so that it is narrowest and lowest at the forward section 30 and increases in width and thickness, or height in a direction towards the rearward section 32. In this manner, the upper part 2 forms a ridge-liked raised portion 34 adapted to the body on the side of the sanitary napkin which is intended to face the user during use. The upper part 2 is attached to the lower part 3 solely at the forward section 30 and the rearward section 32 of the upper part. Since the curvature of the surface 36 of the upper part 2 which faces the lower part 3 is less than the curvature of the surface 37 of the lower part 3 which faces the upper part 2, a gap 38 is created between the upper part and the lower part. The gap 38 allows liquid which is not absorbed by the upper part 2 to be able to flow in under the upper part and to be absorbed by the absorbent body 8 of the lower part 3. In order to be able to maintain the gap 38 between the upper part 2 and the lower part 3 during use, it is necessary that both parts 2, 3 have high stiffness and shape permanence, at least in the region between the upper part's forward and rearward sections 30, 32.

It is not necessary that the gap 38 remains completely unchanged during use. Thus, a certain amount of compression of the upper part and lower part can generally be accepted. It is, however, important that a gap of about 0.5 mm remains under all conditions, at least within the portion of the sanitary napkin which will be initially struck by menstrual blood. This portion is normally termed the wetting region of the sanitary napkin and is indicated by $V_b$ in FIGS. 1 and 2.

Further, it is suitable that the lower part 3, at least in the wetting region $V_b$, is cupped in the transverse direction so that the side edges 14, 16 are somewhat raised from the portion of the lower part 3 which, during use, is positioned directly beneath the upper part 2. By means of such a shaping of the lower part 3, liquid which is not immediately absorbed can be collected in the lower part. If the gap 38 between the upper part 2 and the lower part 3 is relatively small, for example only a millimeter or so, the entire gap can be filled with liquid. This implies that a portion of the liquid can be received by the surface of the upper part 2 facing the lower part.

A suitable size of the gap between the upper part 2 and the lower part 3 has been shown to be between about 0.3 mm and about 5 mm. Suitably, the gap is about 1.5–2 mm. It is not necessary that the sanitary napkin has a gap 38 along the entire length of the upper part 2. For the purposes of the invention, it is sufficient if there is a gap 38 at least in the wetting region $V_b$ of the sanitary napkin.

The absorbent material in the absorbent body 8 of the lower part 3 can be of any suitable type. The absorbent bodies 6, 8 of the upper part 2 and the lower part 3 can thus be of the same or different material or material combinations.

The upper part 2 can be permanently attached to the lower part 3, for example by gluing, welding or stitching. Alternatively, it can be possible to remove the upper part 2 by breaking the joints between the upper part 2 and the lower part 3. It is also conceivable to use fastening means in the form of hook-and-loop type surfaces, resealable lines of adhesive, hooks, crooks, snap fasteners or the like, which permit repeated attachment and separation of an upper part from a lower part. In the latter case, it is possible to imagine that the upper parts are made with different absorption capacities and/or in different shapes and/or sizes. In this manner it is possible for each user to determine herself which upper part best meets her needs.

Figure 3:
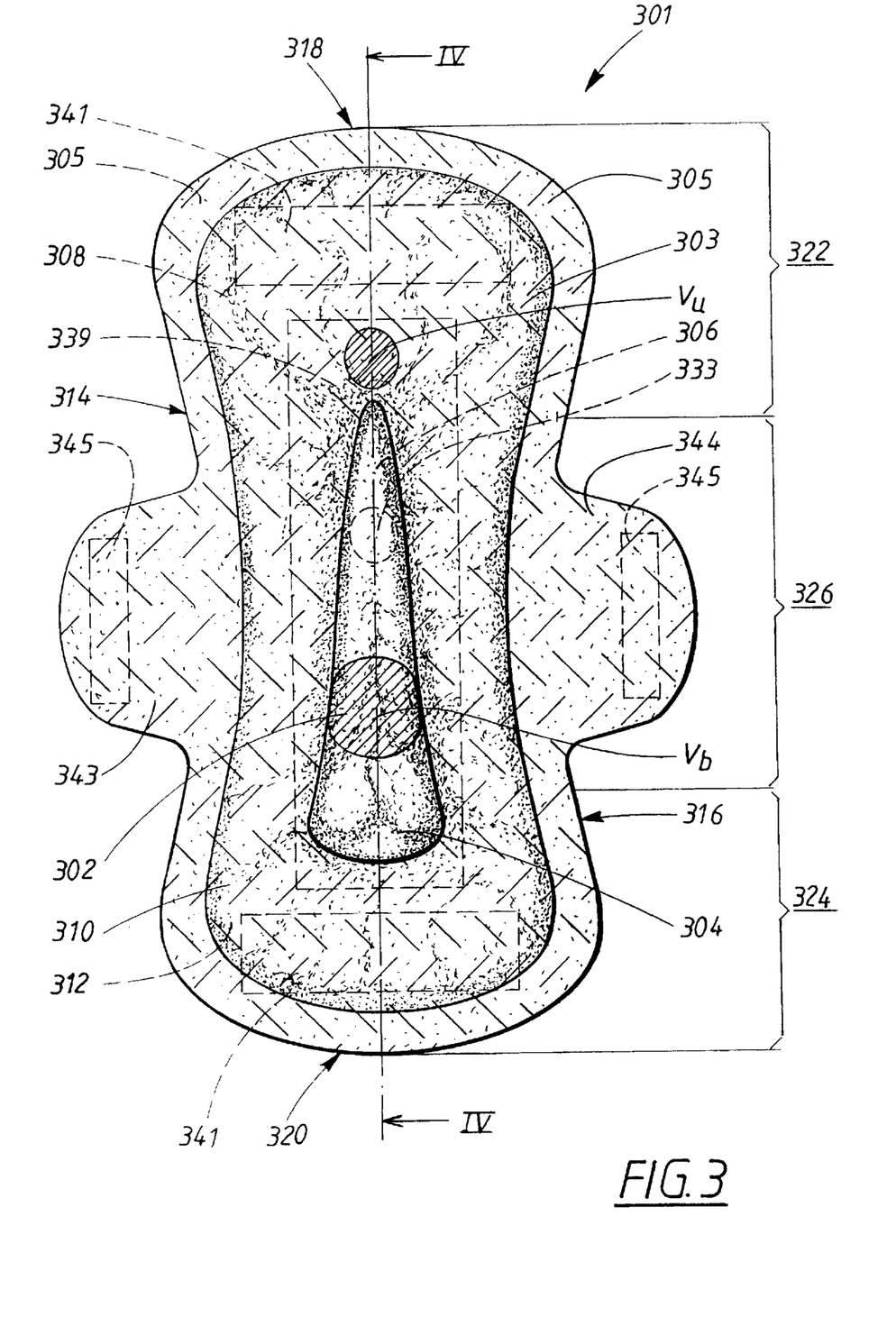
FIG. 3 shows a sanitary napkin according to another embodiment of the invention seen from the side which, during use, is intended to face the user.

It is therefore conceivable that a user initially takes advantage of the possibility to use the sanitary napkin shown in FIGS. 1 and 2 with both the upper part 2 and the lower part 3. Thereafter, the upper part 2 can be released from the lower part 3 and discarded, while the lower part 3 is retained in the panties and used on its own. An incontinence pad 301 is shown in FIG. 3 for female users and is made up of an upper part 302 and a lower part 303. The incontinence pad can advantageously be used as a combined pad for fertile incontinent women during menstruation. The upper part 302 of the incontinence pad facilitates correct placement of the pad in relation to the genitals of the user and provides the pad with good absorption properties for menstruation blood as well.

As with the sanitary napkin 1 shown in FIGS. 1 and 2, the upper part 302 consists of an absorbent body 306 encased in a liquid-permeable wrapping 304. The upper part 302 is additionally shaped in substantially the same manner as the upper part 2 shown in FIGS. 1 and 2.

Figure 4:
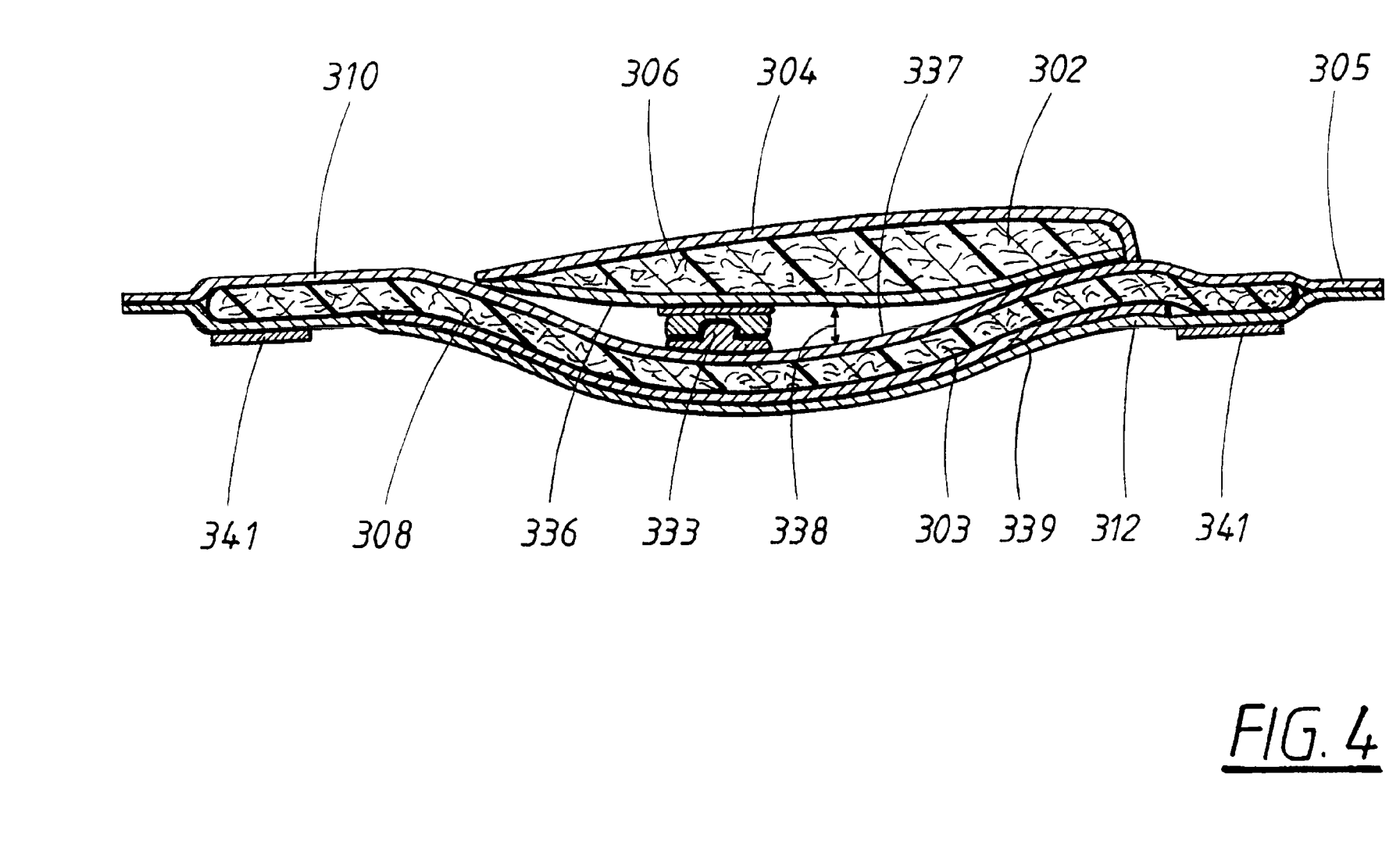
FIG. 4 is a sectional view along line IV—IV through the sanitary napkin of FIG. 3.

The lower part 303 comprises a liquid-permeable surface layer 310, for example of nonwoven material, plastic film or the like, on the surface which faces the upper part. In addition, the lower part has a liquid-impermeable bottom layer 312 on the surface which faces away from the upper part 2. An absorbent body 308 is encased between the liquid-permeable layer 310 and the liquid-impermeable layer 312 by the two layers being mutually joined within an end region 305 about the absorbent body 308.

The incontinence pad 301 is substantially hourglass-shaped with two longitudinally extending side edges 314, 316 and two transversely extending end edges 318, 320. In addition, the incontinence pad 301 has a forward portion 322, a rearward portion 324 and an intermediate narrower mid portion 326.

The upper part 302 of the incontinence pad is attached to the lower part 303 via a snap fastener 333. Thus, one part of the snap fastener 333 is permanently attached to the surface 336 of the upper part 302 which faces the lower part 303, while the other part of the snap fastener is permanently attached to the surface 337 on the lower part 303. The primary function of the snap fastener 333 is of course to retain the upper part 302 on the lower part 303. Since the snap fastener 333 can be unfastened, it is furthermore possible to remove the upper part 302 from the lower part 303 and exchange a used upper part 302 for a new, fresh one. In addition, the snap fastener 333 serves as a spacer between the upper part 302 and the lower part 303 and ensures in this manner that a gap 338 is always present between the two parts 302, 303, at least around the snap fastener 333.

By the use of a spacer, for example a snap fastener 333, it is possible to make the upper part and the lower part from less stiff material than is the case for the sanitary napkin shown in FIGS. 1 and 2. Nevertheless, it is highly desirable that at least the upper part 302 be sufficiently stiff to substantially retain its shape during use. In particular, it is unsuitable for the upper part 302 to buckle or fold during use.

The incontinence pad shown in FIGS. 3 and 4 is provided with a stiffening insert 339 of rectangular shape and is arranged between the liquid-impermeable bottom layer 312 and the absorbent body 308 of the lower part 303. The insert 339 has a somewhat greater planer extension than the upper part 302 and is placed so that no part of the upper part 302 projects beyond the edges of the insert 339. The primary function of the insert 339 is to create a shape-permanent, liquid-receiving bowl in the mid portion 326 of the incontinence pad 301. As is most clearly visible, the insert 339 is curved, preferably in both the longitudinal and the transverse direction, so that it creates a cupped cavity between both parts 302, 303 of the incontinence pad. When the incontinence pad 301 is used as a combined menstruation/incontinence pad, bodily fluid will strike the incontinence pad at two different wetting regions $V_u$, $V_b$. Thus the pad will be wetted by menstruation blood in the wetting region $V_b$ which, during use, is arranged at the user's vaginal opening, while urine will strike the pad in the wetting region $V_u$ located further forward on the incontinence pad.

In order to be able to be attached to a pair of panties, the incontinence pad 301 is provided with attachment means in the form of transversely located, rectangular adhesive regions 341. The adhesive regions 341 are arranged on the liquid-impermeable bottom layer 302 in the forward portion 322 and rearward portion 326 of the incontinence pad. Naturally, it is of course possible to use different adhesive patterns instead, such as longitudinally extending regions, stripes, dots, or the like. Instead of adhesive attachment means, it is also possible to use a friction coating such as a foam plastic layer, a rubber coating or the like.

The incontinence pad further comprises an attachment flap 343, 344 arranged on each side edge 314, 316 immediately adjacent the mid portion 326 of the incontinence pad. The attachment flaps 343, 344 are also provided with attachment means in the form of adhesive regions 345. During use, the attachment flaps 343, 344, also, are intended to be folded about the leg edges of the user's panties and attached using the adhesive regions 345 on the outside of the panties.

Figure 5:
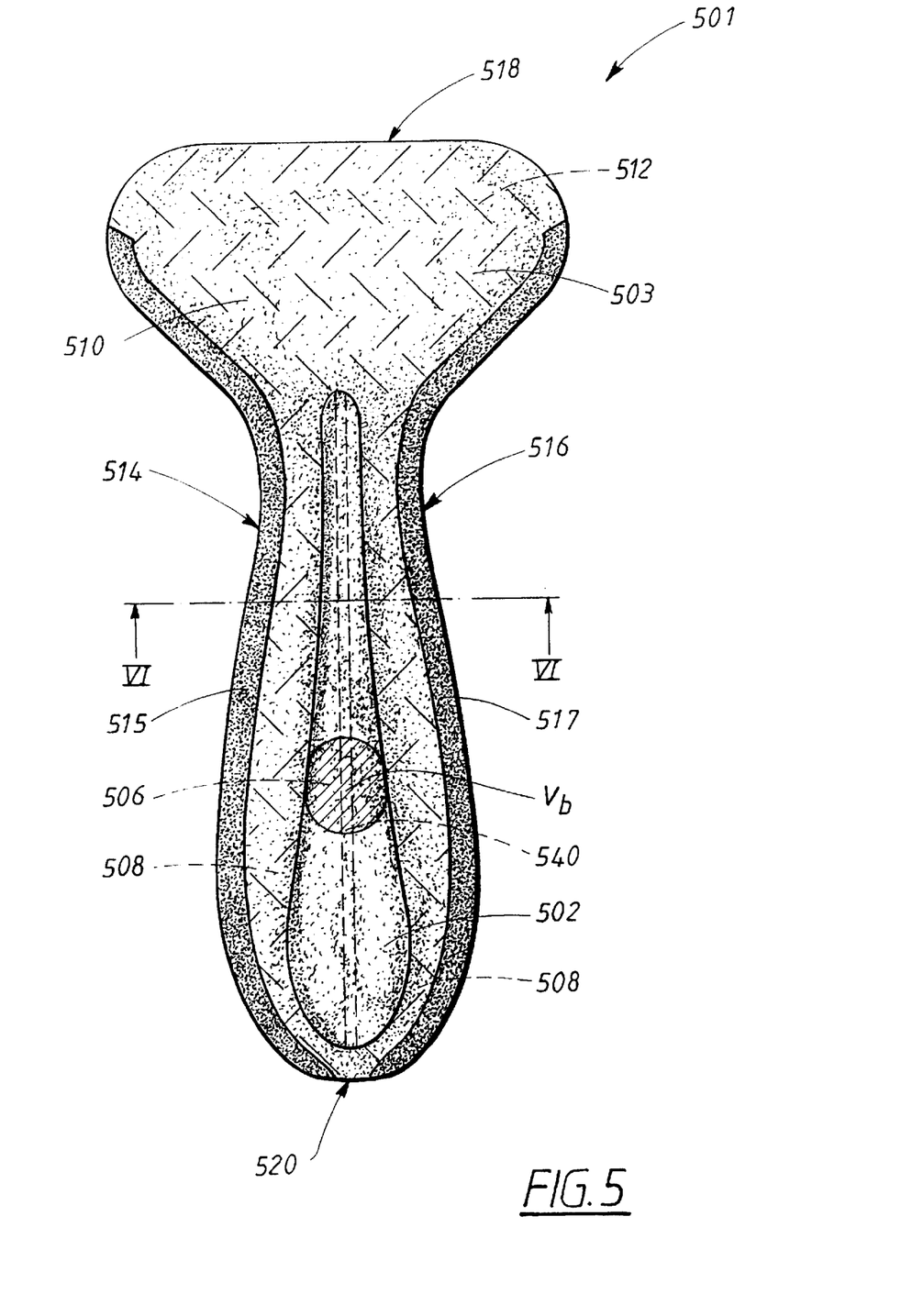
FIG. 5 shows a sanitary napkin according to a further embodiment of the invention seen from the side which, during use, is intended to face the user.
Figure 6:
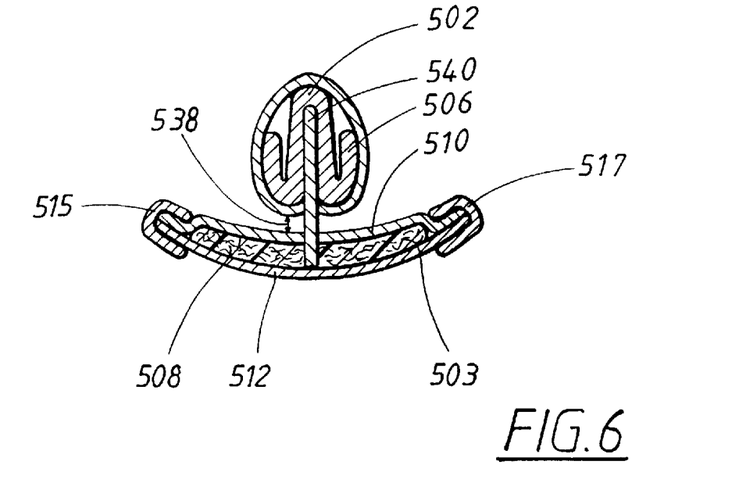
FIG. 6 is a cross-sectional view along line VI—VI through the sanitary napkin of FIG. 5.

A sanitary napkin 501 is shown in FIGS. 5 and 6 having substantially the same construction as the sanitary napkin 1 in FIGS. 1 and 2. The numbering of the various parts of the sanitary napkin in FIGS. 5 and 6 is therefore analogous with that which was used for the description of the sanitary napkin in FIGS. 1 and 2. The sanitary napkin 501 shown in FIG. 5 does, however, differ in two respects from the previously described sanitary napkin 1.

Along each longitudinally extending side edge 514, 516, the sanitary napkin 501 is provided with soft padded strips 515, 517. The padded strips 515, 517 suitably consist of foam plastic, fibre wadding or laminate comprising such soft, pressure absorbing material. The strips 515, 517 are folded around the side edges 515, 517 and serve as pressure-absorbing deformation zones.

Figure 7:
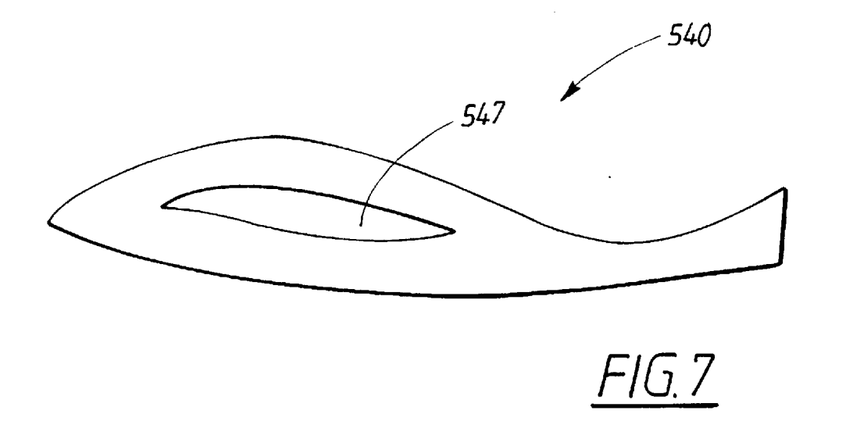
FIG. 7 shows a stiffening-element for use in the sanitary napkin of FIGS. 5 and 6.
Figure 8:
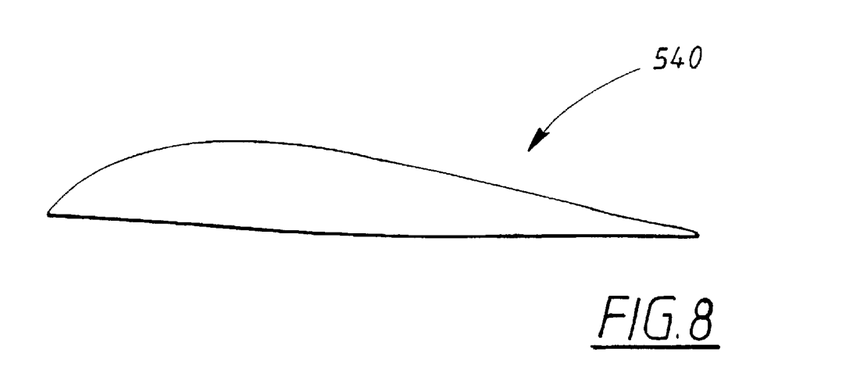
FIG. 8 shows an alternative embodiment of a stiffening-element for the sanitary napkin of FIGS. 5 and 6.

In addition, the sanitary napkin comprises a longitudinally extending stiff insert 540 in the form of a plate which is arranged substantially perpendicular to the shape-retaining liquid-impermeable bottom layer 512 of the lower part 503. Such an insert is described in detail in Swedish patent application no. 9604225-4. Suitable inserts are flat material pieces made for example from plastic and advantageously having a thickness between 0.2 mm and 2 mm. In addition, it is possible to make the insert from metal, wood or similar very stiff materials. A plastic material which is somewhat resilient when the upper part is subjected to compression in the plane of the insert 540 is however preferred. In order to further increase the resiliency of the insert 540, it can be provided with some type of deformation zone, for example a recess of the type which is shown in FIG. 7, a material weakening or a fold precursor. An insert 540 according to an alternative embodiment is shown in FIG. 8.

As is most readily apparent from FIG. 6, the absorbent body 506 in the upper part 502 consists of an absorbent layer folded in the longitudinal direction, made for example of the fibre material described in WO 94/10953 or WO 94/10956. The absorbent body 506 is suspended over the insert 540 projecting from the bottom layer 512. A liquid-permeable wrapping 504 encases the absorbent body 506 and maintains the fold in the absorbent material.

The stiff insert 540 is attached to the liquid-impermeable bottom layer 512 in the lower part 503, for example by gluing or welding or by being moulded or in another way made in one piece with the bottom layer 512. The insert extends from the bottom layer 512, up through the absorbent body 508 in the lower part 503 and through the liquid-permeable surface layer 512 of the lower body and thereafter up into the upper part 502.

By means of the stiffness of the insert 540, it is possible to maintain a gap 538 during use between the upper part 502 and the lower part 503. Thus, the insert 540 acts as a spacer between the upper part 502 and the lower part 503. Even when the insert 540 is of the type shown in FIG. 7, it must be sufficiently shape-permanent for a gap 538 of 0.5 mm to remain between both parts 502, 503 of the sanitary napkin even during maximum compression of the parts parallel to the plane of the insert 540.

The invention is not to be regarded as being restricted to the embodiments described herein. Instead, a number of further variations and modifications are conceivable within the scope of the appended claims. Furthermore, all possible combinations of the described embodiments are intended to be covered by the invention.

What is claimed is:

1. An absorbent article having a longitudinal direction and a transverse direction and comprising a mid portion and two end portions, which article is adapted to be substantially accommodated within a user's panties, the absorbent article comprising an absorbent upper part and an absorbent lower part, which two parts are mutually joined, whereby the upper part presents a first liquid-permeable surface which, during use, faces the user and a second surface which faces towards a first liquid-permeable surface on the lower part, the lower part further presenting a second, liquid-impermeable surface on a side of the article which, during use, faces away from the user, wherein the article further comprises means for obtaining and maintaining an elongate cavity between the second surface of the upper part and the first surface of the lower part, at least in the mid portion of the article, whereby the upper part and the lower part in the elongate cavity are mutually separated by a predetermined distance of between 0.3 and 5 mm, the distance being maintained during use of the article irrespective of a user's posture, and the elongate cavity permits at least some liquid to flow from the user into the elongate cavity without first passing through other components of the article.

2. The absorbent article according to claim 1, wherein the upper part is substantially made from relatively stiff material and is substantially elongate and has a first end section and a second end section, wherein the upper part is attached to the lower part solely at the end sections, and wherein the lower part comprises a rigid, shape-permanent material layer which has at least the same extension in a principal plane of the article as the upper part, wherein the shape-permanent material layer is curved in the longitudinal direction of the article in a direction away from the upper part, wherein the first surface of the lower part is also curved in a direction away from the upper part, and wherein the second surface of the upper part has a shape such that the article has the cavity between the upper part and the lower part.

3. The absorbent article according to claim 2, wherein the shape-permanent material layer is curved in a direction away from the upper part in both the longitudinal and the transverse direction of the article, wherein the lower part is bowl-shaped, at least in the mid portion of the article.

4. The absorbent article according to claim 2, wherein the shape-permanent material layer forms the liquid-impermeable surface of the lower part and thereby forms a liquid-impermeable bottom layer of the article.

5. The absorbent article according to claim 2, wherein the shape-permanent material layer at least somewhere within the mid portion of the article has a greatest extension in the transverse direction of the article which does not exceed 40 mm.

6. The absorbent article according to claim 5, wherein the article comprises two longitudinally extending side edges and two transversely extending end edges, wherein soft, pressure-absorbing deformation zones are arranged at least along parts of the side edges.

7. The absorbent article according to claim 1, wherein a spacer is arranged between the upper part and the lower part.

8. The absorbent article according to claim 7, wherein the spacer is a snap fastener.

9. The absorbent article according to claim 7, wherein the spacer is a stiffening-element arranged substantially perpendicular to a bottom layer of the lower part, wherein the element extends from the bottom layer through the lower part and into the upper part.

10. The absorbent article according to claim 1, wherein the upper part is fixedly attached to the lower part.

11. The absorbent article according to claim 1, wherein the upper part is releasably attached to the lower part.

12. The absorbent article according to claim 10, wherein the connection between the upper part and the lower part permits repeated attachment and separation of the two parts.

13. The absorbent article according to claim 1, wherein the upper part has an extension in the transverse direction of the article which is less than the extension of the lower part in the transverse direction.

14. The absorbent article according to claim 13, wherein the width of the upper part in the mid portion is between ¼ and ⅓ of the width of the lower part.

15. The absorbent article according to claim 1, wherein the upper part has an extension in the longitudinal direction of the article which is less than the extension in the longitudinal direction of the lower part.

16. The absorbent article according to claim 15, wherein the length of the upper part is between ⅓ and ¾ of the length of the lower part.

17. The absorbent article as in claim 1, wherein the absorbent article is a sanitary napkin, incontinence pad, or panty liner.

18. The absorbent article as in claim 5, wherein the width of the shape-permanent material layer in the mid portion of the article is at most 35 mm.

19. An absorbent article comprising:
a mid portion and two end portions;
an absorbent lower part having a first liquid-permeable surface facing a user during use, and a second liquid-impermeable surface on a side of the article which faces away from the user during use;
an absorbent upper part having a forward edge defining a forward section, a rearward edge defining a rearward section, two side edges, a first liquid-permeable surface which faces the user during use, and a second surface which faces the first liquid-permeable surface of the absorbent lower part;
the second surface of the upper part and the first liquid-permeable surface of the lower part defining an elongate cavity in the mid portion of the article;
the absorbent upper part and the absorbent lower part being sufficiently shape-permanent in a region between the forward section and the rearward section so as to maintain a distance of between 0.3 and 5 mm between the second surface of the upper part and the first liquid-permeable surface of the lower part in the elongate cavity during use irrespective of a user's posture;
the upper part and the lower part being joined solely at the forward section and rearward section of the upper part so as to keep the side edges of the upper part at a distance from the lower part so as to enable liquid transmission into the cavity; and
wherein the absorbent article is adapted to be substantially accommodated within a user's panties.

20. An absorbent article comprising:
a mid portion and two end portions;
an absorbent lower part having a first liquid-permeable surface facing a user during use;
a substantially elongate absorbent upper part having a forward edge defining a forward section, a rearward edge defining a rearward section, two side edges, a first liquid-permeable surface which faces the user during use, and a second surface which faces the first liquid-permeable surface of the absorbent lower part, the upper part comprising relatively stiff material;
the absorbent lower part further having a rigid, shape-permanent liquid-impermeable surface on a side of the article which faces away from the user during use, the rigid, shape permanent liquid-impermeable surface extending at least to the edges of the upper part in longitudinal and transverse directions;

the first liquid-permeable surface of the lower part being curved in a direction away from the upper part;

the rigid, shape-permanent liquid-impermeable surface being curved in the longitudinal direction away from the the upper part and having a shape so as to form an elongate cavity between the second surface of the upper part and the first liquid-permeable surface; and the absorbent upper part and the absorbent lower part being sufficiently shape-permanent in a region between the forward section and the rearward section so as to maintain a distance of between 0.3 and 5 mm between the second surface of the upper part and the first liquid-permeable surface of the lower part in the elongate cavity during use; and the upper part and the lower part being joined solely at the forward section and the rearward section of the upper part so as to keep the side edges of the upper part at a distance from the lower part so as to enable liquid transmission into the cavity;

wherein the absorbent article is adapted to be substantially accommodated within a user's panties.

21. The absorbent article according to claim 20, wherein the rigid, shape-permanent liquid-impermeable surface is curved in a direction away from the upper part in both a longitudinal and a transverse direction of the article, and wherein the absorbent lower part is bowl-shaped in at least the mid portion of the article.

22. The absorbent article according to claim 20, wherein the rigid, shape-permanent liquid-impermeable surface has a width of 40 mm at most in the mid portion of the article.

23. The absorbent article as in claim 22, wherein the width of the rigid, shape-permanent liquid-impermeable surface is 35 mm at most in the mid portion of the article.

24. The absorbent article according to claim 23, wherein the article comprises two longitudinally extending side edges and two transversely extending end edges, wherein soft, pressure-absorbing deformation zones are arranged at least along parts of the side edges.

25. The absorbent article according to claim 19, wherein the forward and rearward sections of the upper part are attached to the lower part with a snap fastener.

26. The absorbent article according to claim 19, wherein the absorbent upper part is fixedly attached to the absorbent lower part.

27. The absorbent article according to claim 19, wherein the absorbent upper part is releasably attached to the absorbent lower part.

28. The absorbent article according to claim 19, wherein the absorbent upper part and the absorbent lower part are joined with an attachment device which permits repeated attachment and separation of the upper and lower parts.

29. The absorbent article according to claim 19, wherein the upper part has a width which is less than a width of the lower part.

30. The absorbent article according to claim 29, wherein the width of the upper part in the mid portion is between 1/4 and 1/3 of the width of the lower part.

31. The absorbent article according to claim 19, wherein the upper part has a length less than a length of the lower part in the longitudinal direction.

32. The absorbent article according to claim 31, wherein the length of the upper part is between 1/3 and 3/4 of the length of the lower part.

33. The absorbent article as in claim 19, wherein the absorbent article is a sanitary napkin, incontinence pad, or panty liner.

34. An absorbent article comprising:

a mid portion and two end portions;

an absorbent lower part having a first liquid-permeable surface facing the user during use;

an absorbent upper part having a forward section, a rearward section, side edges, a first liquid-permeable surface which faces the user during use and a second surface which faces towards the first liquid-permeable surface on the absorbent lower part;

the absorbent lower part further having a second liquid-impermeable surface on a side of the article which faces away from the user during use;

the second surface of the upper part and the first liquid-permeable surface of the lower part defining an elongate cavity in the mid portion of the article, the upper part and the lower part being sufficiently shape-permanent so as to maintain a distance of between 0.3 and 5 mm between the second surface of the upper part and the first liquid-permeable surface of the lower part in the elongate cavity during use;

the article further comprising a stiffening element disposed between the upper and lower parts so as to keep the side edges of the upper part at a distance from the lower part so as to enable liquid transmission into the cavity, the stiffening element being arranged substantially perpendicular to a bottom layer of the lower part and extending from the bottom layer of the lower part through the lower part and into the upper part;

wherein the absorbent article is adapted to be substantially accommodated within a user's panties.

35. The absorbent article according to claim 34, wherein the upper part has a width which is less than a width of the lower part.

36. The absorbent article according to claim 35, wherein the width of the upper part in the mid portion is between 1/4 and 1/3 of the width of the lower part.

37. The absorbent article according to claim 34, wherein the upper part has a length which is less than a length of the lower part.

* * * * *